(12) United States Patent
O'Brien et al.

(10) Patent No.: US 10,034,642 B1
(45) Date of Patent: Jul. 31, 2018

(54) WHEEL ALIGNMENT GUIDE FOR MEDICAL EQUIPMENT AND METHOD OF USE

(71) Applicants: Graig Thomas O'Brien, Tampa, FL (US); Jon Kimball, Tampa, FL (US)

(72) Inventors: Graig Thomas O'Brien, Tampa, FL (US); Jon Kimball, Tampa, FL (US)

(73) Assignee: The Parking Space, LLC, Tampa, FL (US)

( * ) Notice: Subject to any disclaimer, the term of this patent is extended or adjusted under 35 U.S.C. 154(b) by 0 days.

(21) Appl. No.: 15/853,296

(22) Filed: Dec. 22, 2017

(51) Int. Cl.
*A61B 6/00* (2006.01)
*G01B 11/275* (2006.01)
*A61B 6/04* (2006.01)

(52) U.S. Cl.
CPC .......... *A61B 6/4405* (2013.01); *A61B 6/0407* (2013.01); *A61B 6/587* (2013.01); *G01B 11/275* (2013.01); *G01B 2210/303* (2013.01)

(58) Field of Classification Search
CPC ........... A61B 6/04; A61B 6/0407; A61B 6/44; A61B 6/4405; A61B 6/08; A61B 6/10; A61B 6/102; A61B 6/105; A61N 5/10; A61N 2005/10
See application file for complete search history.

(56) References Cited

U.S. PATENT DOCUMENTS

| | | | | |
|---|---|---|---|---|
| 2,355,066 A * | 8/1944 | Goldfield et al. | ... | A61B 6/4405 33/1 A |
| 4,935,949 A * | 6/1990 | Fujita | ...................... | A61B 6/035 378/198 |
| 5,339,350 A * | 8/1994 | Thelosen | ............. | A61B 6/4405 378/194 |
| 5,873,144 A * | 2/1999 | Tupper | ...................... | B60B 7/02 16/18 CG |
| 6,678,917 B1 * | 1/2004 | Winters | .................... | B60B 7/00 16/18 CG |
| 8,558,204 B2 * | 10/2013 | Rees | ...................... | A61B 6/107 250/516.1 |
| 2010/0150304 A1 * | 6/2010 | Kawamura | ............ | A61B 6/032 378/9 |
| 2011/0174997 A1 * | 7/2011 | Rees | ...................... | A61B 6/107 250/516.1 |
| 2017/0215985 A1 * | 8/2017 | Kubiak | .................. | A61B 90/39 |

* cited by examiner

*Primary Examiner* — Thomas R Artman
(74) *Attorney, Agent, or Firm* — Paul Murty; Smith & Hopen, P.A.

(57) ABSTRACT

A wheel alignment guide that provides a visual indication of the desired placement of an apparatus. The wheel alignment guide includes a body having an opening disposed therein. The wheel alignment guide is configured to surround a portion of the apparatus, such as a wheel, via the opening. In addition, the wheel alignment guide is adapted to rest on a ground surface, being held in place via a charge, such as an electrostatic charge created by static cling vinyl. A wheel of a medical device is disposed within the opening of the wheel alignment guide after a desired position of the medical device is selected. If the medical device is moved during a medical procedure, the medical device may be repositioned due to the placement of the wheel alignment guide. Accordingly, the wheel alignment guide eliminates the need for inefficient markers and potentially-dangerous adhesives, particularly in an operating room.

20 Claims, 3 Drawing Sheets

WHEEL ALIGNMENT GUIDE FOR MEDICAL EQUIPMENT AND METHOD OF USE

BACKGROUND OF THE INVENTION

1. Field of the Invention

This invention relates, generally, to a wheel alignment guide and a method of use. More specifically, it relates to a wheel alignment guide for use with medical equipment in an operation room, such that medical professionals can correctly align medical equipment with respect to the patient's body.

2. Brief Description of the Prior Art

It is important to correctly position medical equipment according to the needs of a medical procedure. For example, a fluoroscopy machine must align with a patient at a particular angle to scan a target area. To correctly align with patients having different body types and characteristics, equipment often must be repositioned. In addition, during a medical procedure, a medical professional may need to move the equipment away from the patient, thereby allowing unobstructed access to the patient. The equipment must then be repositioned to be used on the patient. In the case of a fluoroscopy machine, the angle must match the initial angle; otherwise, the machine will provide an incorrect scan of the target area, which can cause complications to the procedure.

Currently, medical professionals use a variety of indicators to guide machine realignment. One method of providing a visual indication is to mark the floor with a marker, highlighter, or other writing implement. By marking the floor in such a way, a medical professional can generally guide a machine to its initial position. However, marking the floor does not represent an ideal solution. For example, there is a possibility that the mark will be erased during a procedure. In addition, if the machine must be repositioned to accommodate multiple patients, different marks will be placed on the floor. The marks are not only aesthetically unpleasant, but also increase the likelihood that an incorrect mark will be chosen.

Another method of providing a visual indication is to use an adhesive to mark the correct spot. However, adhesives also suffer from several drawbacks, making their use a less-than-ideal solution. For example, adhesives may leave remnant residue on the floor that can cause misalignment of machinery, as well as present a danger to machinery and personnel if the floor is sticky. In addition, the use of adhesives may cause bacterial or fungal growth in an otherwise sterile environment. Organism growth can cause medical complications for the patient and other personnel within the room, particularly during a surgical procedure. As such, adhesives used within a sterile environment can put the patient and others at risk of infection and other diseases and disorders.

Accordingly, what is needed is a device and method of aligning medical equipment, allowing the equipment to be moved and repositioned during a medical procedure. However, in view of the art considered as a whole at the time the present invention was made, it was not obvious to those of ordinary skill in the field of this invention how the shortcomings of the prior art could be overcome.

BRIEF SUMMARY OF THE INVENTION

The long-standing but heretofore unfulfilled need for a wheel alignment guide for use with medical equipment in an operation room is now met by a new, useful, and nonobvious invention.

The novel structure includes a body made of a flexible material, such as static cling vinyl. The body includes a top side opposite a bottom side, with the top and bottom sides being separated by an outer edge. The outer edge may taper from the bottom side to the top side, such that the bottom side has a greater surface area than the top side. The bottom side is configured to rest on a ground surface. In an embodiment, the bottom side securely couples to the ground surface via an electrostatic connection. Alternatively, the bottom side includes a magnetic or electric charge, forming a connection with a complementary charge on the ground surface.

The body includes an opening extending therethrough from the top side to the bottom side. The opening is cross-shaped, including a first portion that is perpendicular to a second portion. The first and second portions intersect at their respective midpoints, forming a cross-shape. The first and second portions are connected through a plurality of concave interior edges on the body.

A slit is disposed within the body and extends therethrough from the top side to the bottom side. The slit forms a channel with one of the first portion and the second portion of the opening. The body is adapted to separate at the slit, such that first member and second member of the body are formed separated by the slit. The first and second members are configured to receive oppositely-directed forces, which expand a width of the slit, such that the width of the slit is greater than a width of a wheel of a medical device.

The slit thereby creates a passageway for the wheel of a medical device. The width of the slit is configured to expand, making the width of the slit greater than the width of the wheel. The slit thereby enables the wheel alignment guide to be deployed around the wheel. In the deployed configuration, the opening receives the wheel, after the wheel passes through the slit. One of the first and second portions of the opening receives the wheel, and the wheel is capable of rotatably translating within the opening between the first and second portions. The plurality of concave interior edges allow the wheel to pivot without obstruction between the first and second portions.

A novel method of aligning a wheel of a medical device includes the step of positioning a medical device on a ground surface. The medical device includes at least one wheel in communication with the ground surface. The wheel allows the medical device to translate along the ground surface.

The method next includes the step of surrounding the wheel with a wheel alignment guide. The wheel alignment guide is adapted to separate at the slit, whereby the slit has a width that is greater than a width of the wheel. The slit is in communication with an opening disposed within the wheel alignment guide, with the slit creating a passage for the wheel to enter the opening. The opening is cross-shaped and is partially defined by a plurality of concave interior edges on the wheel alignment guide. After the opening of the wheel alignment guide receives the wheel, the wheel alignment guide is disposed on the ground surface. The method includes the step of pivoting the wheel between a first and a second portion of the opening. The wheel is capable of pivoting without obstruction as a result of the plurality of concave interior edges.

In a further step, the medical device is translated along the ground surface in a direction away from the wheel alignment guide. The wheel alignment guide remains at its original position. After translating the medical device away from the wheel alignment guide, the medical device is repositioned within the wheel alignment guide. During this step, the wheel of the medical device is disposed within the opening of the wheel alignment guide, thereby returning the medical device to its initial and desired position.

An object of the invention is to provide visual identification of the correct placement of a medical device. The invention utilizes a novel wheel alignment guide that eliminates the need to use inefficient markers or potentially-harmful adhesives. Using the wheel alignment guide allows for the repositioning of the medical device, improving the efficiency and safety of a medical procedure.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a wheel alignment guide and methods of use. The wheel alignment guide is configured to rest on a ground surface and provide a stationary visual indicator for the positioning of a medical device. In addition, the wheel alignment guide is adapted to aid in the repositioning of the medical device such that a position can be replicated after the medical device has been moved. The wheel alignment guide allows a medical professional to move a medical device away from a patient, and later accurately replicate the original position of the medical device, eliminating the need for inefficient markers and potentially-dangerous adhesives.

Figure 1:
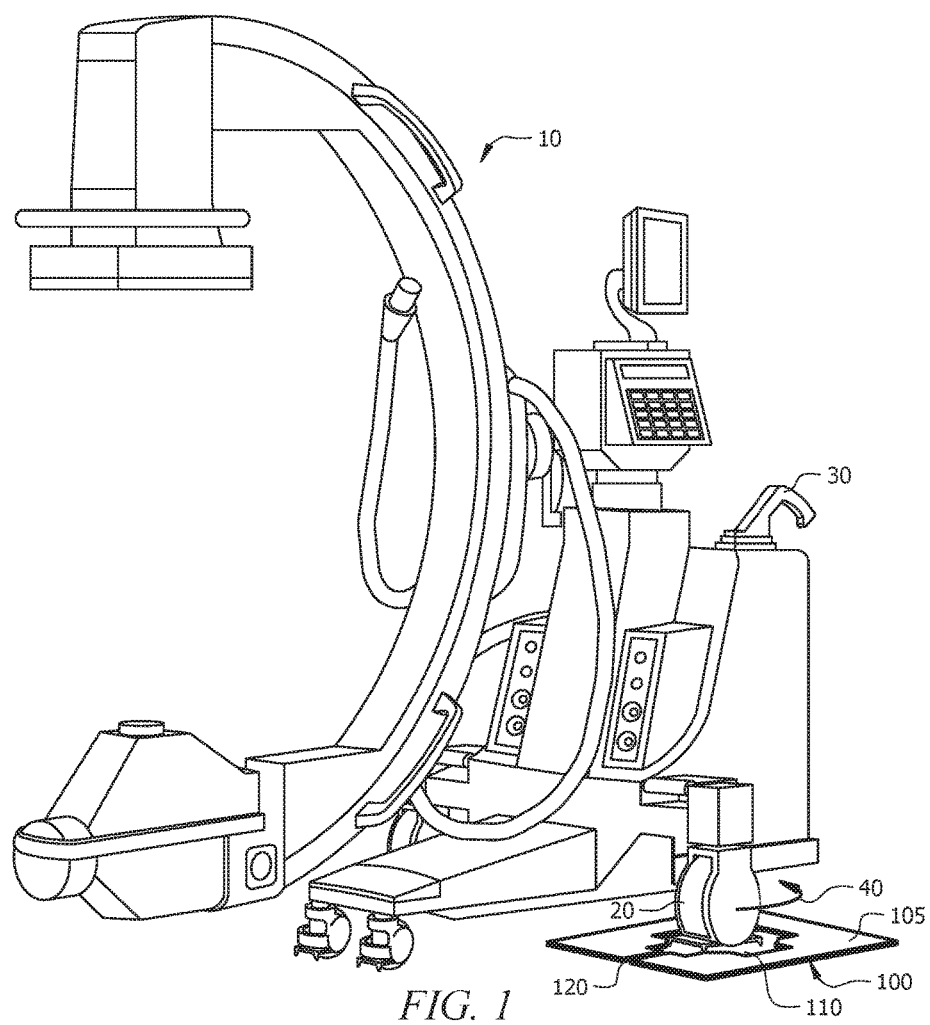
FIG. 1 is a perspective view of a wheel alignment guide used in combination with a medical device having a wheel, in accordance with an embodiment of the present invention.

As shown in FIG. 1, an embodiment of wheel alignment guide 100, adapted to be used in combination with medical device 10, is shown in detail. Medical device 10 includes at least one wheel 20, and is configured to translate along a ground surface via wheel 20. Wheel 20 is actuated by handle 30, with handle 30 configured to rotatably translate wheel 20 with respect to the ground surface. The rotational translation of wheel 20 is generally denoted as reference numeral 40. Medical device 10 is depicted as a fluoroscopy machine; however, it is appreciated that other movable devices may be used in combination with wheel alignment guide 100.

Wheel alignment guide 100 includes body 105, which includes opening 110 and slit 120. Opening 110 is adapted to receive wheel 20 of medical device 10, as shown in FIG. 1. As such, wheel alignment guide 100 is configured to surround wheel 20 of medical device 10. Wheel alignment guide 100 thereby is adapted to serve as a visual indicator for a position of medical device 10. For example, if medical device 10 is axially translated along the ground surface, medical device 10 can be repositioned in its original position by disposing wheel 20 within opening 110 of wheel alignment guide 100.

Body 105 of wheel alignment guide 100 is made of a material that is capable of being sterilized for use within an operating room. In an embodiment, wheel alignment guide 100 is packaged in a sterile, single-use, disposable packaging prior to being used in the operating room. The material of wheel alignment guide 100 is flexible, allowing body 105 to bend and deform about opening 110. To aid in the deformation, wheel alignment guide 100 includes slit 120 disposed within body 105. Slit 120 separates first member 105a from second member 105b of body 105 (the relationship between slit 120 and first and second member 105a, 105b is shown in greater detail in FIGS. 2-3). Slit 120 is in communication with opening 110, creating a channel between opening 110 and the environment exterior to wheel alignment guide 100. Slit 120 is thereby a passageway for wheel 20. During deployment of wheel alignment guide 100, oppositely-directed forces are applied onto first member 105a and second member 105b of body 105 to expand the width of slit 120. As such, the width of slit 120 is greater than the width of wheel 20, thereby enabling wheel alignment guide 100 to be deployed around wheel 20. In the deployed configuration, opening 110 receives wheel 20, after wheel 20 passes through slit 120.

Figure 2:
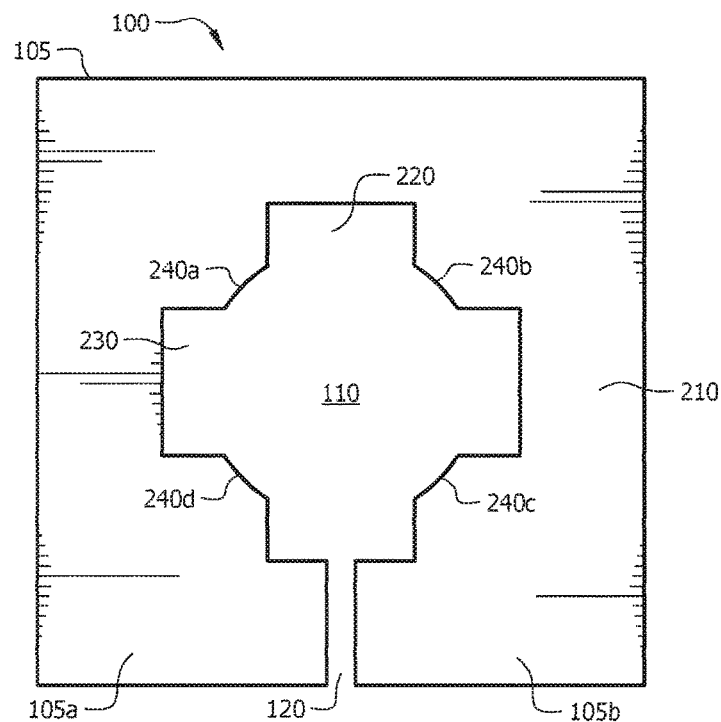
FIG. 2 is a bottom plan view of the wheel alignment guide of FIG. 1.

Wheel alignment guide 100 is shown in greater detail in FIG. 2, which represents a bottom plan view. Body 105 of wheel alignment guide 100 includes bottom side 210. Bottom side 210 is configured to rest on a ground surface when wheel alignment guide 100 is in use. It is important that wheel alignment guide 100 remains substantially stationary on the ground surface, since wheel alignment guide 100 is used to accurately align medical device 10. If wheel alignment guide 100 translates along the ground surface, it will be difficult to correctly align medical device 10. Accordingly, in an embodiment, bottom side 210 includes a charge that is adapted to form a connection with a complementary charge of the ground surface. For example, the charge may be a magnetic charge that is adapted to magnetically couple with a corresponding magnet disposed on or within the ground surface. Alternatively, the charge may be an electric charge that is adapted to electrically couple with a corresponding charge of the ground surface. In an alternative embodiment, bottom side 210 is made of a static cling vinyl material that is adapted to securely couple to the ground surface. The static cling vinyl material allows bottom side 210 to adhere to the ground surface via electrostatic forces, rather than adhesives. It is appreciated that alternative materials may be used to form bottom side 210, so long as the materials are adapted to form a connection with the ground surface. Regardless of the method, bottom side 210 rests on and secures to the ground surface to maintain a chosen position of wheel alignment guide 100.

Opening 110 is also shown in greater detail in FIG. 2. Opening 110 is shown as being cross-shaped, including first portion 220 and second portion 230. First portion 220 and second portion 230 intersect at their respective midpoints to from the cross-shape. First and second portions 220, 230 are each sized to receive wheel 20 of medical device 10. Opening 110 is partially defined by a plurality of concave interior edges 240a, 240b, 240c, 240d, each of which is disposed adjacent to both first and second portions 220, 230. Thus, first and second portions 220, 230 are connected through the plurality of concave interior edges 240a-d. Opening 110 is in communication with the environment exterior to wheel alignment guide 100 through slit 120, which forms a channel between the exterior environment and opening 110. FIG. 2 depicts slit 120 being in communication with first portion 220; however, it is appreciated that slit 120 may alternatively be in communication with second portion 230, or with one of the plurality of concave interior edges 240a-d. Moreover, FIG. 2 depicts slit 120 as an air-space disposed within body 105, separating first member 105a and second member 105b of body 105. However, it is appreciated that first member 105a and second member 105b may be disposed substantially adjacent to one another, such that slit 120 is not noticeable until body 105 is deformed and first and second members 105a, 105b are separated from each other. Additionally, while FIG. 2 depicts one slit 120 disposed within body 105, it is appreciated that more than one slit 120 may be formed within body 105 and in communication with opening 110.

In use, opening 110 is configured to receive wheel 20 of medical device 30 within one of first portion 220 and second portion 230. For example, FIG. 1 depicts wheel 20 being disposed within first portion 220. However, opening 110 is designed to allow for the rotational translation of wheel 20 within opening 110. Wheel 20 can be pivoted between being disposed within first portion 220 and second portion 230. The plurality of concave interior edges 240a-d are sized, shaped, and positioned to allow wheel 20 to pivot between first portion 220 and second portion 230. The plurality of concave interior edges 240a-d thereby provide and path via which wheel 20 can rotatably translate between first and second portions 220, 230, without obstacle or interruption. Such an unimpeded path is an important feature of wheel alignment guide 100, because an obstacle could make medical device 10 unstable and prone to tipping.

Figure 3:
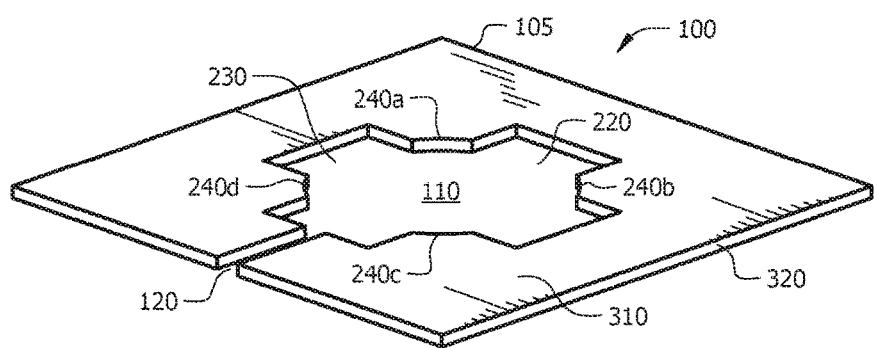
FIG. 3 is a perspective view of the wheel alignment guide of FIG. 1.

Turning now to FIG. 3, wheel alignment guide 100 is shown in a top-side perspective view. Body 105 of wheel alignment guide 100 includes top side 310, which is opposite bottom side 210 (shown in FIG. 2 and described above). FIG. 3 shows that opening 110 is a through opening within body 105. Similarly, slit 120 is a through opening within body 105. Accordingly, wheel alignment guide 100 can receive wheel 20 by wrapping around and surrounding wheel 20 through slit 120 and opening 110, without obstruction from an intermediary material.

FIG. 3 depicts top side 310 and bottom side 210 having substantially identical surface areas, with top and bottom sides 310, 210 being separated by edge 320. Medical device 10 can translate along the ground surface and overcome edge 320 and top side 310 to dispose wheel 20 within opening 110, similar to a vehicle overcoming a speed bump. However, it is appreciated that top side 310 may have a smaller surface area than bottom side 210. Accordingly, edge 320 may be tapered from bottom side 210 to top side 310, such that the surface area of top side 310 is smaller than that of bottom side 210 by a factor determined by the taper. The use of a tapered edge 320 may facilitate the translation of medical device 10, since wheel 20 would have a shortened distance to overcome edge 320.

Figure 4:
FIG. 4 is a flow chart diagram describing a method of aligning a wheel of a medical device, in accordance with the present invention.

Referring now to FIG. 4, in conjunction with FIGS. 1-3, an exemplary process-flow diagram is provided, depicting a method of aligning a wheel of a medical device. The steps delineated in the exemplary process-flow diagram of FIG. 4 are merely exemplary of an order of aligning a wheel of a medical device. The steps may be carried out in another order, with or without additional steps included therein.

The method of aligning a wheel of a medical device begins at step 400, during which medical device 10 is positioned on a ground surface. Medical device 10 includes at least one wheel 20, allowing medical device 10 to be translated along the ground surface. As such, a medical professional can move medical device 10 around an operating room.

The positioning of medical device 10 is often integral to the success of a medical procedure. For example, if medical device 10 is a fluoroscopy machine, the angle of the machine in relation to the patient is a vital component of the medical procedure. Depending on the requirements of a particular medical procedure, or the varying body characteristics between patients, medical device 10 may be moved away from its initial position. Failure to replicate the initial position after medical device 10 has been moved can cause a failure of the procedure, or medical complications. Accordingly, step 410 includes surrounding wheel 20 of medical device 10 with wheel alignment guide 100. To deploy wheel alignment guide 100, a user applies oppositely-directed forces onto first and second members 105a, 105b of body 105. The application of the oppositely-directed forces extends the width of slit 120, such that the width of slit 120 is greater than the width of wheel 20, thereby enabling deployment of wheel alignment guide 100. In the deployed configuration, one of first portion 220 and second portion 230 of opening 110 is longitudinally-aligned with wheel 20. Next, the method proceeds to step 420, which includes disposing wheel 20 within opening 120. Slit 120 creates a passageway for wheel 20. Opening 110 receives wheel 20 after wheel 20 passes through the passageway created by slit 120.

After surrounding wheel 20 with wheel alignment guide 100, the method proceeds to step 430, during which wheel alignment guide 100 is disposed on the ground surface. Wheel alignment guide 100 thereby serves as a visual indication of the desired position of medical device 10, in the event that medical device 10 is translated away from the desired position. Wheel alignment guide 100 secures to the ground surface during step 430, making it difficult to inadvertently disconnect wheel alignment guide 100 from the ground surface. For example, if wheel alignment guide 100 is made of a static cling vinyl material, wheel alignment guide 100 forms an adhesive-like relationship with the ground surface via an electrostatic connection. Alternatively, wheel alignment guide 100 may form an electric or magnetic connection with a complementary charge on the ground surface.

The method may then proceed to step 440, during which wheel 20 is pivoted within wheel alignment guide 100.

Depending on the requirements of the medical procedure, it may be desirable to orient wheel 20 in a direction parallel to handle 30, or perpendicular to handle 30. By pivoting wheel 20 to different orientations, medical device 10 may be translated in different directions. Due to the plurality of concave interior edges 240a-d discussed above, wheel alignment guide 100 facilitates the pivoting of wheel 20 between orientations.

During step 450, medical device 10 is translated away from wheel alignment guide 100. As discussed above, it may be necessary to move medical device 10 away from its desired position. For example, a surgeon may require access to a patient that is blocked by the desired position of medical device 10. Alternatively, the area around medical device 10 may require cleaning between medical procedures. In such a situation, it is desirable to move medical device 10 away from wheel alignment guide 100, with wheel alignment guide 100 remaining in the desired position. Accordingly, during step 460, wheel 20 is repositioned within wheel alignment guide 100 in the desired position of medical device 10. In step 460, a user translates medical device 10 toward wheel alignment guide 100, which remains located in its initial position throughout the medical procedure. Wheel alignment guide 100 receives wheel 20 of medical device 10, thereby repositioning wheel 20 within wheel alignment guide 100, returning medical device 10 to its initial and desired location. Wheel alignment guide 100 thereby ensures that medical device 10 is correctly repositioned, increasing the likelihood success of the medical procedure.

It is appreciated that alternative embodiments of wheel alignment guide 100 may be used as visual indicators for the placement of non-medical devices. For example, wheel alignment guide 100 may be used to efficiently store and item within an enclosed space, such as a garage, such that the item can easily be restored to a desired position. Similarly, wheel alignment guide 100 may be used with a device that does not include traditional wheels, so long as the device is movable. For example, an operating table including stationary legs may need to be placed in a particular spot within an operating room. Accordingly, wheel alignment guide 100 may be used to surround a stationary leg on the table to provide a visual indication of the current placement of the table.

Glossary of Claim Terms

Charge: is a physical property of a material that causes the material to experience a force when disposed proximate to a complementary charge. For example, a charge may be an electrostatic charge, electric charge, or magnetic charge.

Flexible: as used herein, "flexible" means capable of bending or folding without breaking.

Ground surface: is a surface upon which human beings can stand and equipment can rest. For example, a ground surface may be a floor of an operating room.

Medical device: is an apparatus or machine used in furtherance or aid of a medical procedure. For example, a medical device may be a fluoroscopy machine used to scan a patient during surgery.

Static cling vinyl: is a vinyl material capable of coupling to a surface via an electrostatic charge.

Taper: as used herein, "taper" means to gradually become smaller toward an end.

Wheel: is a substantially rounded structure capable of lateral translation along a ground surface. The wheel may be a swivel caster, rigid caster, alloy wheel, bicycle wheel, omni wheel, or the like, and may be made of plastic, rubber, cast iron, aluminum, stainless steel, polyurethane, or any other material capable of lateral translation.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A wheel alignment guide comprising:
   a body having a top side opposite a bottom side, the bottom side configured to rest on a ground surface, the body including an opening extending therethrough from the top side to the bottom side;
   the opening being cross-shaped, including a first portion perpendicular to a second portion, the first and second portions intersecting at their respective midpoints, the first and second portions connected through a plurality of concave interior edges on the body;
   wherein the opening is configured to receive a wheel of a medical device within one of the first portion and the second portion; and
   wherein the plurality of concave interior edges are adapted to allow the wheel of the medical device to pivot between the first portion of the opening and the second portion of the opening.

2. The wheel alignment guide of claim 1, wherein:
   the body is of a flexible static cling vinyl material that is adapted to securely couple to the ground surface via an electrostatic connection.

3. The wheel alignment guide of claim 1, further comprising:
   a slit disposed within the body and extending therethrough from the top side to the bottom side, the slit forming a channel with one of the first portion and the second portion of the opening.

4. The wheel alignment guide of claim 3, wherein:
   the body is adapted to separate at the slit, wherein the slit is configured to permit the wheel of the medical device to pass therethrough, thereby enabling the wheel to enter the opening.

5. The wheel alignment guide of claim 1; wherein:
   at least one of the first portion and the second portion of the opening is sized to receive the wheel of the medical device.

6. The wheel alignment guide of claim 1, wherein:
   the body includes an outer edge that tapers from the bottom side to the top side, such that the bottom side has a greater surface area than the top side.

7. The wheel alignment guide of claim 1, wherein:
   the bottom side of the body has a charge, the bottom side being adapted to form a connection with a complementary charge of the ground surface.

8. The wheel alignment guide of claim 7, wherein:
   the charge is a magnetic charge, and the bottom side is adapted to magnetically couple with a corresponding magnet on the ground surface.

9. The wheel alignment guide of claim 7, wherein:
   the charge is an electric charge, and the bottom side is adapted to electrically couple with the ground surface.

10. A method of aligning a wheel of a medical device, the method comprising:
- positioning a medical device on a ground surface, the medical device having at least one wheel in communication with the ground surface;
- surrounding the at least one wheel of the medical device with a wheel alignment guide by passing the at least one wheel through a slit disposed within the wheel alignment guide, the slit creating a passage to an opening disposed within the wheel alignment guide;
- receiving the at least one wheel within the opening; and
- disposing the wheel alignment guide on the ground surface;
- wherein the opening is cross-shaped, including a first portion perpendicular to a second portion, the first and second portions intersecting at their respective midpoints, the first and second portions connected through a plurality of concave interior edges on the body.

11. The method of aligning a wheel of a medical device of claim 10, wherein:
- the at least one wheel is disposed within one of the first portion and the second portion of the opening.

12. The method of aligning a wheel of a medical device of claim 11, further comprising the step of:
- pivoting the at least one wheel from being disposed within one of the first and second portion to being disposed within the other of the first and second portion, the at least one wheel translating along at least two of the plurality of concave interior edges on the body during the pivoting step.

13. The method of aligning a wheel of a medical device of claim 10, further comprising the steps of:
- translating the medical device along the ground surface in a direction away from the wheel alignment guide; and
- after translating the medical device away from the wheel alignment guide, repositioning the medical device within the wheel alignment guide by disposing the at least one wheel within the opening of the wheel alignment guide.

14. The method of aligning a wheel of a medical device of claim 10, wherein:
- the wheel alignment guide is of a flexible static cling vinyl material; and
- during the step of disposing the wheel alignment guide on the ground surface, the wheel alignment guide forms an electrostatic with the ground surface via the static cling vinyl material.

15. The method of aligning a wheel of a medical device of claim 10, wherein:
- during the step of disposing the wheel alignment guide on the ground surface, the wheel alignment guide forms a magnetic connection with a complementary magnet disposed on the ground surface.

16. The method of aligning a wheel of a medical device of claim 10, wherein:
- during the step of disposing the wheel alignment guide on the ground surface, the wheel alignment guide from an electrical connection with a complementary charge within the ground surface.

17. A wheel alignment guide comprising:
- a body having a top side opposite a bottom side, the bottom side configured to rest on a ground surface, the body including an opening extending therethrough from the top side to the bottom side;
- a slit disposed within the body and extending therethrough from the top side to the bottom side, the slit in communication with the opening;
- wherein the opening is configured to receive a wheel of a medical device; and
- whereby the slit is configured to permit the wheel to pass therethrough, thereby enabling the opening to receive the wheel.

18. The wheel alignment guide of claim 17, wherein:
the body is of a flexible static cling vinyl material that is adapted to securely couple to the ground surface via an electrostatic connection.

19. The wheel alignment guide of claim 17, wherein:
the opening is cross-shaped, including a first portion perpendicular to a second portion, the first and second portions intersecting at their respective midpoints, the first and second portions connected through a plurality of concave interior edges on the body;
whereby the plurality of concave interior edges are adapted to allow the wheel of the medical device to pivot between the first portion of the opening and the second portion of the opening.

20. The wheel alignment guide of claim 17, wherein:
the body is adapted to separate at the slit into a first member and a second member, the first and second members configured to receive oppositely-directed forces, thereby expanding a width of the slit, such that the width of the slit is greater than a width of the wheel.

* * * * *